United States Patent
Buehler et al.

(10) Patent No.: US 7,632,244 B2
(45) Date of Patent: Dec. 15, 2009

(54) TAMPER EVIDENT TIP CAP ASSEMBLY

(75) Inventors: John Buehler, Bridgeton, NJ (US); Brian Gatton, Elmer, NJ (US); David Manera, Petersburg, NJ (US)

(73) Assignee: Comar, Inc., Buena, NV (US)

( * ) Notice: Subject to any disclaimer, the term of this patent is extended or adjusted under 35 U.S.C. 154(b) by 291 days.

(21) Appl. No.: 11/501,782

(22) Filed: Aug. 10, 2006

(65) Prior Publication Data
US 2008/0097310 A1 Apr. 24, 2008

(51) Int. Cl.
*A61M 5/00* (2006.01)
*B65D 39/00* (2006.01)
*B65D 41/00* (2006.01)
*B65D 43/00* (2006.01)
*B65D 47/00* (2006.01)
*B65D 51/00* (2006.01)
*B65D 85/00* (2006.01)

(52) U.S. Cl. .................. 604/111; 604/110; 215/228; 206/726

(58) Field of Classification Search ............... 644/111, 644/110; 215/251, 256, 235
See application file for complete search history.

(56) References Cited

U.S. PATENT DOCUMENTS

| | | | |
|---|---|---|---|
| 3,923,185 A | 12/1975 | Choksi et al. | |
| 4,667,837 A * | 5/1987 | Vitello et al. | 215/228 |
| 4,709,823 A * | 12/1987 | Beck et al. | 215/235 |
| 4,929,232 A * | 5/1990 | Sweeney et al. | 604/111 |
| 5,328,474 A * | 7/1994 | Raines | 604/110 |
| 5,711,443 A * | 1/1998 | Bennett | 215/256 |
| 5,738,220 A * | 4/1998 | Geszler | 206/726 |
| 5,989,227 A * | 11/1999 | Vetter et al. | 604/232 |
| 6,520,935 B1 * | 2/2003 | Jansen et al. | 604/111 |
| 6,846,303 B2 | 1/2005 | Eakins et al. | |
| 2004/0064095 A1 * | 4/2004 | Vitello | 604/111 |
| 2004/0116858 A1 * | 6/2004 | Heinz et al. | 604/111 |
| 2004/0225258 A1 * | 11/2004 | Balestracci | 604/111 |

* cited by examiner

*Primary Examiner*—Nicholas D Lucchesi
*Assistant Examiner*—Ian K Holloway
(74) *Attorney, Agent, or Firm*—James G. O'Boyle

(57) ABSTRACT

A tamper evident tip cap assembly for a prefilled dosage syringe having a tip cap wherein a sleeve is frangibly connected to the tip cap, and is captured within an overcap freely rotatable thereon. The tamper evident tip cap assembly is removed from the syringe tip cap by pulling the overcap to break the frangible connection between the sleeve and syringe tip cap.

3 Claims, 2 Drawing Sheets

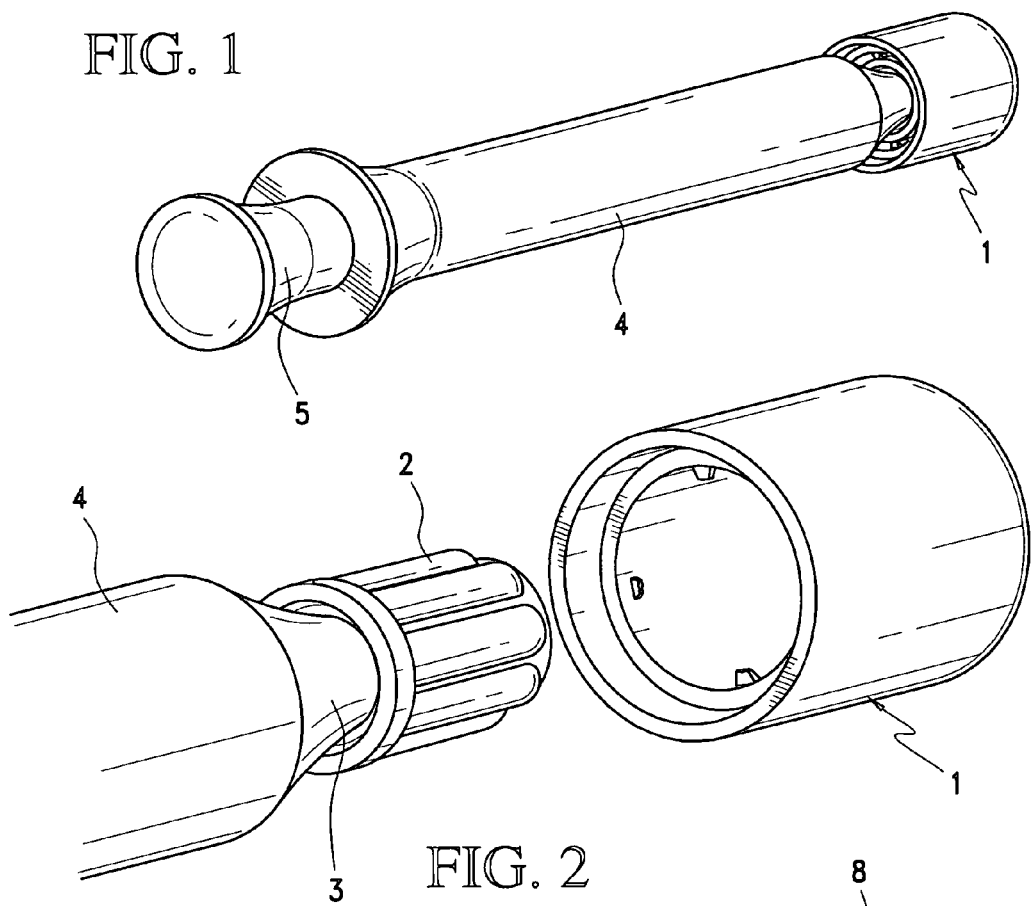
FIG. 1
FIG. 2
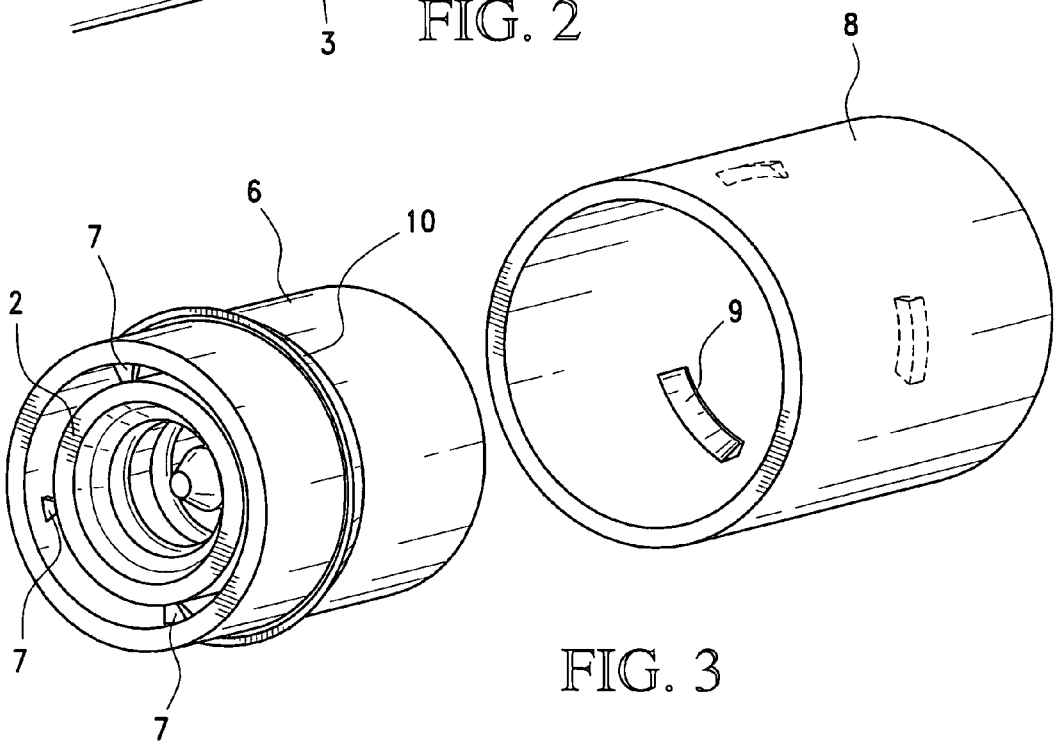
FIG. 3

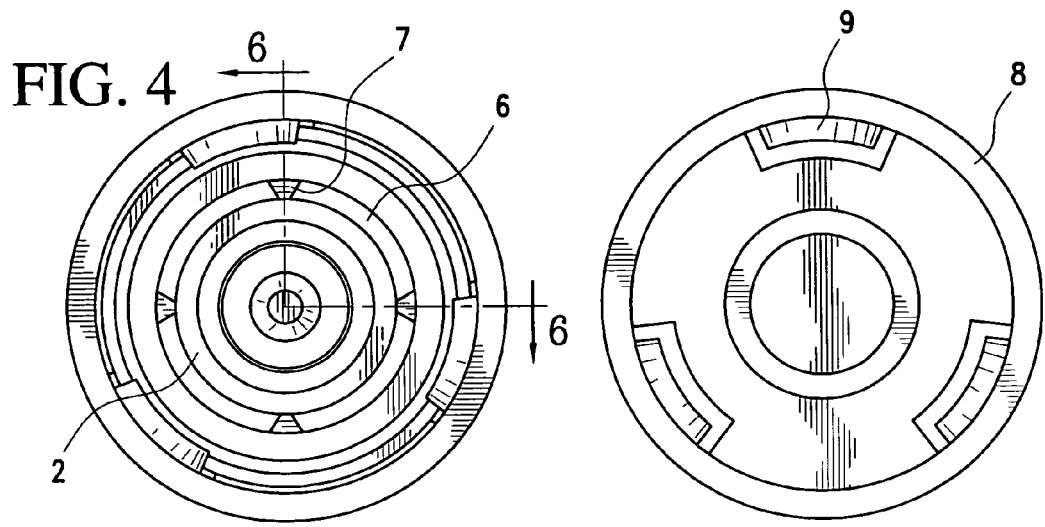
FIG. 4
FIG. 5
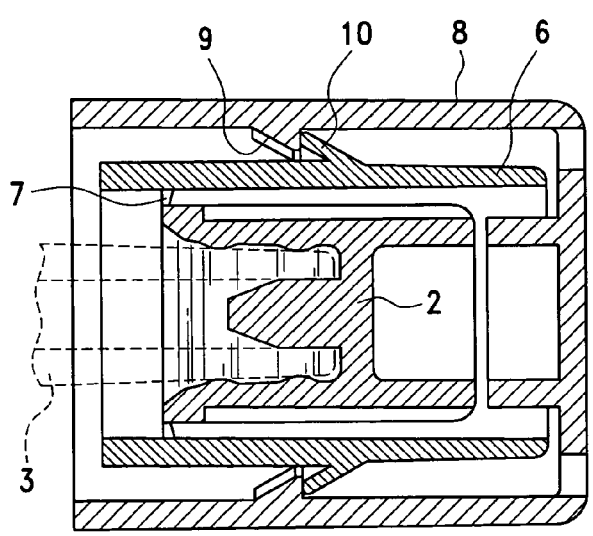
FIG. 6
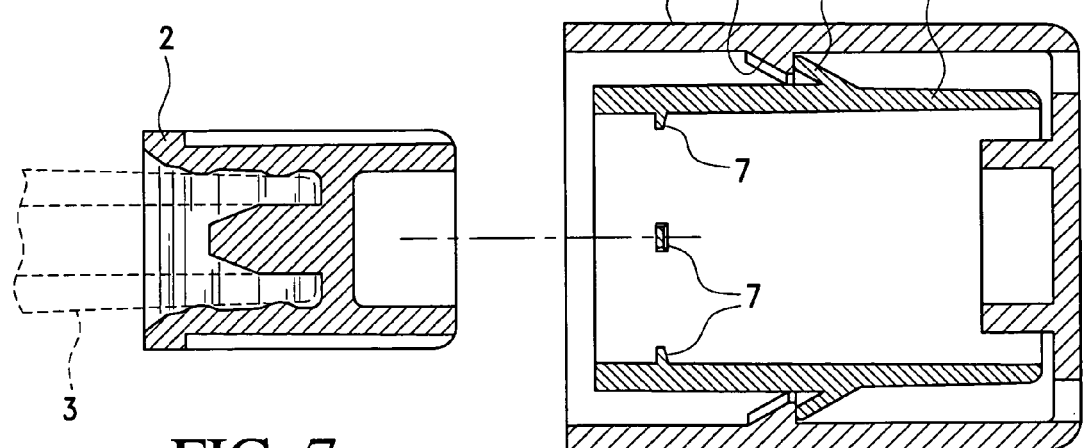
FIG. 7

TAMPER EVIDENT TIP CAP ASSEMBLY

BACKGROUND OF THE INVENTION

Conventional prefilled dosage syringes include a barrel, a plunger slidably mounted in the barrel, and a tip cap for sealing the medication in the barrel. The sealed prefilled dosage syringe is often times stored for long periods of time until it is needed. In order to be sure that the integrity of the tip cap seal has not been compromised, some prefilled dosage syringes are provided with tamper evident indicators, which included visible tear strips or frangible connections between the tip cap and a cover, or collar, on the syringe barrel.

SUMMARY OF THE INVENTION

The tamper evident tip cap assembly of the present invention comprises, essentially, a sleeve surrounding a prefilled dosage syringe tip cap and spaced radially outwardly therefrom. The sleeve is connected to the tip cap by a plurality of radially extending circumferentially spaced frangible connectors, and an overcap is freely rotatable on the sleeve. The open end portion of the overcap is provided with a plurality of circumferentially spaced, radially inwardly extending lugs adapted to engage a radially outwardly extending flange, integral with the outer wall surface of the sleeve, whereby the overcap is removed from the syringe tip cap by pulling the overcap to abut the lugs against the flange on the sleeve until the frangible connectors break, whereby the overcap and captured sleeve are removed from the syringe tip cap.

BRIEF DESCRIPTION OF THE DRAWINGS

FIG. 1 is a perspective view of a prefilled dosage syringe having the tamper evident tip cap assembly of the present invention mounted thereon;

FIG. 2 is an exploded view showing the tamper evident tip cap assembly, shown in FIG. 1, removed from the syringe tip cap;

FIG. 3 is a perspective view of the components employed in the tamper evident tip cap assembly of the present invention;

FIG. 4 is an end elevational view of the tamper evident tip cap assembly of the present invention;

FIG. 5 is an end view of the overcap employed in the tamper evident tip cap assembly of the present invention;

FIG. 6 is a sectional side elevational view of the tamper evident tip cap assembly connected to a syringe tip cap; and FIG. 7 is a sectional side elevational view showing the tamper evident tip cap assembly removed from the syringe tap cap.

DETAILED DESCRIPTION OF THE PREFERRED EMBODIMENT

Referring to the drawings, and more particularly to FIGS. 1 and 2, the tamper evident tip cap assembly 1 of the present invention is adapted to be connected to a tip cap 2 mounted on the discharge end 3 of a conventional prefilled dosage syringe having a barrel 4 and a plunger 5 slidably mounted therein.

As will be seen in FIGS. 3 and 6, the tamper evident tip cap assembly 1 comprises a sleeve 6 surrounding the syringe tip cap 2 and spaced radially outwardly therefrom. The sleeve 6 is connected to the syringe tip cap 2 by a plurality of radially extending circumferentially spaced, flangible connectors 7.

An overcap 8 is mounted concentrically with the sleeve 6 and freely rotatable thereon by a plurality of radially inwardly extending, circumferentially spaced lugs 9 integral with the inner wall surface of the overlap 8 and engaging a radially outwardly extending flexible flange 10 integral with the outer wall surface of the sleeve 6.

The lugs 9 and flexible flange 10 have cooperating inclined surfaces so that the overcap 8 can be slid onto the sleeve 6 in such a manner that the lugs 9 compress the flexible inclined flange 10 which snaps behind the lugs 10, to thereby capture the sleeve 6, whereby the overcap 8 is freely rotatable thereon.

To remove the tamper evident tip cap assembly 1 from the syringe tip cap 2, the overcap 8 is pulled in a direction whereby the lugs 9 thereon abut the flange 10 on the sleeve 6 to thereby break the frangible connections 7 between the sleeve 6 and the syringe tip cap 2.

It is to be understood that the form of the invention herewith shown and described is to be taken as a preferred example of the same, and that various changes in the shape, size and arrangement of parts may be resorted to, without departing from, the spirit of the invention or scope of the subjoined claims.

We claim:

1. A tamper evident tip cap assembly for a dosage syringe having a barrel, a plunger slidably mounted in said barrel, a discharge end on the barrel and a tip cap sealing adapted to seal the discharge end on said barrel, said tamper evident tip cap assembly being mounted on said tip cap and comprising a sleeve mounted concentrically with on said tip cap and spaced radially outwardly therefrom, frangible means integrally connecting said sleeve to said tip cap, and a cylindrical overcap mounted concentrically with said sleeve and spaced radially outwardly therefrom and non-frangible connector means extending between the sleeve and the overcap whereby the sleeve is captured within the overcap which is freely rotatable in each direction on the sleeve, said non-frangible connector means comprising a plurality of radially inwardly extending, circumferentially spaced lugs integral with the inner wall surface of said overcap and engaging a radially outwardly extending flexible flange integral with the outer wall surface of the sleeve, whereby the tamper evident tip cap assembly is removed from the syringe tip cap by pulling the overcap and associated sleeve, to thereby break the frangible connection between the sleeve and the syringe tip cap.

2. A tamper evident tip cap assembly according to claim 1, wherein the frangible means comprises a plurality of radially extending circumferentially spaced frangible connectors.

3. A tamper evident tip cap assembly according to claim 1, wherein the lugs and flexible flange have cooperating inclined surfaces to facilitate the assembling of the overcap on the sleeve.

* * * * *